(12) United States Patent
Bhalla

(10) Patent No.: US 7,732,476 B2
(45) Date of Patent: Jun. 8, 2010

(54) LEUKEMIA TREATMENT METHOD AND COMPOSITION

(75) Inventor: Kapil N Bhalla, Tampa, FL (US)

(73) Assignee: University of South Florida, Tampa, FL (US)

( * ) Notice: Subject to any disclaimer, the term of this patent is extended or adjusted under 35 U.S.C. 154(b) by 128 days.

(21) Appl. No.: 11/307,298

(22) Filed: Jan. 31, 2006

(65) Prior Publication Data

US 2007/0072839 A1    Mar. 29, 2007

Related U.S. Application Data

(63) Continuation of application No. PCT/US2004/024774, filed on Aug. 2, 2004.

(60) Provisional application No. 60/481,163, filed on Jul. 31, 2003.

(51) Int. Cl.
*A01N 43/56* (2006.01)
*A61K 31/40* (2006.01)

(52) U.S. Cl. .................................................. 514/408

(58) Field of Classification Search ....................... None
See application file for complete search history.

(56) References Cited

U.S. PATENT DOCUMENTS

| | | | |
|---|---|---|---|
| 6,004,565 A | 12/1999 | Chiba et al. | |
| 6,187,543 B1 | 2/2001 | Blackshear | |
| 6,552,065 B2 | 4/2003 | Remiszewski et al. | |
| 7,276,612 B2 | 10/2007 | Verner et al. | |
| 2003/0096875 A1 | 5/2003 | Burton et al. | |
| 2004/0152632 A1 | 8/2004 | Feingold | |
| 2004/0180911 A1 | 9/2004 | Capraro et al. | |
| 2005/0020570 A1 | 1/2005 | Griffin et al. | |

FOREIGN PATENT DOCUMENTS

| | | |
|---|---|---|
| EP | 0 919 244 A2 | 6/1999 |
| WO | WO 02/22577 | 3/2002 |
| WO | WO 2004/052292 | 6/2004 |

OTHER PUBLICATIONS

Weisberg et. al., Cancer Cell, Jun. 2002, 1:433-443.*
Gura, Science, 1997, 278:1041-1042.*
Johnson, British Journal of Cancer, 2001, 84:1424-1431.*
Bali et al., "Superior Activity of the Combination of Histone Deacetylase Inhibitor LAQ824 and the FLT-3 Kinase Inhibitor PKC412 against Human Acute Myelogenous Leukemia Cells with Mutant FLT-3," Clinical Cancer Research, 2004, pp. 4991-4997, vol. 10.
Remiszewski et al., N-Hydroxy-3-phenyl-2-propenamides as Novel Inhibitors of Human Histone Deacetylase with in Vivo Antitumor Activity: Discovery of (2E)-N-Hydroxy-3-[4-[[(2-hydroxyethyl)[1H-indol-3-yl)ethyl]amino]methyl]-phenyl]-2-propenamide (NVP-LAQ824), J. Med. Chem., 2003, pp. 4609-4624, vol. 46.
Lee et al., "Parallel Phase I Studies of Daunorubicin Given With Cytrabine and Etoposide With or Without the Multidrug Resistance Modulator PCS-833 in Previously Untreated Patents 60 years or Age or Older With Acute Myeloid Leukemia: Results of Cancer and Leukemia Group B Study 9420," Journal of Clinical Oncology, 1999, pp. 2831-2839, vol. 17, No. 9.
Raffa et al., "Unexpected And Pronounced Antinociceptive Synergy Between Spinal Acetaminophen (Paracetamol) and Phentolamine," European Journal of Pharmacology, 2001, pp. R1-R2, vol. 412.
Tallarida, "The Interaction Index: A Measure Of Drug Synergism," Pain, 2002, pp. 163-168, vol. 98.
Tallarida et al., "Antinociceptive Synergy, Additivity, and Subadditivity with Combinations of Oral Glucosamine Plus Nonopioid Analgesics In Mice," Journal of Pharmacology and Experimental Therapeutics, 2003, pp. 699-704, vol. 307, No. 2.
Tanda et al., "Combinations of Cocaine With Other Dopamine Uptake Inhibitors: Assessment of Additivity," Journal of Pharmacology and Experimental Therapeutics, Fast Forward, 2009, First published on May 29, 2009; DOI: 10.1124/jpet.109.154302.

* cited by examiner

*Primary Examiner*—Frederick Krass
*Assistant Examiner*—Marcos Sznaidman
(74) *Attorney, Agent, or Firm*—Bryan Cave LLP

(57) ABSTRACT

A method of inducing high anti-leukemia activity responsive to the combination of hydroxamic acid analogue histone deacetylase inhibitors and PKC412 against human acute leukemia characterized as expressing phosphorylated (p)FLT3 kinase by a novel flow cytometry-based assay.

4 Claims, 9 Drawing Sheets

LEUKEMIA TREATMENT METHOD AND COMPOSITION

CROSS REFERENCE TO RELATED APPLICATIONS

This application is a continuation of PCT Application No. PCT/US2004/024774, filed Aug. 2, 2004, which claims benefit of U.S. Provisional Application No. 60/481,163, filed Jul. 31, 2003.

BACKGROUND OF THE INVENTION

This invention relates to the use of high anti-leukemia activity responsive to the combination of hydroxamic acid analogue histone deacetylase inhibitors and PKC412 against human acute leukemia characterized as expressing phosphorylated (p)-FLT3 kinase by a novel flow cytometry based assay.

The majority of the patients with Acute Myeloid Leukemia (AML) are incurable with current forms of chemotherapy. In approximately 25% of AML the leukemia cells express a constitutively active form of auto-phosphorylated (p) FLT3 tyrosine kinase on the cell surface. The activity of p-FLT3 confers growth and survival advantage on the leukemic cells. Patients with acute leukemia, whose leukemia cells express p-FLT3 kinase activity, have a poor overall clinical outcome. PKC412 is a novel staurosporine analogue that inhibits p-FLT3 kinase activity and induces apoptosis (programmed cell death) of the leukemic cells. Although treatment with PKC412 results in the inhibition of p-FLT3 kinase activity, it fails to eradicate the leukemia cells and achieve durable clinical benefit. Therefore, it would be desirable to potently downmodulate the levels and activity of pFLT3 in leukemia cells to achieve maximum anti-leukemia effect. This effect would only be observed in those leukemia patients whose leukemia cells possess p-FLT3 kinase activity.

Therefore, to improve the overall benefit of the treatment strategies based on PKC412, it is important to identify those patients whose leukemia cells possess p-FLT3 kinase activity. So far the assays that have been employed to identify these patients have been cumbersome and slow, and difficult to implement in the clinical setting.

Accordingly, what is needed is a flow cytometry-based assay that would rapidly identify patients with acute leukemia, whose blasts possess surface expression of active p-FLT3.

SUMMARY OF INVENTION

One embodiment of the present invention comprises a method of treating cancer comprising the steps of contacting a target cell with a therapeutically effective amount of a histone deacetylase inhibitor and concomitantly contacting the target cell with a therapeutically effective amount of a tyrosine kinase inhibitor. In this embodiment, the type of cancer being treated is acute myeloid leukemia wherein the target cells express the constitutively active mutant or wild type autophosphorylate (p) FLT-3 tyrosine kinase. The histone deacetylase inhibitor is a cinnamyl hydroxamate analogue, such as LAQ824. The tyrosine kinase being inhibited is FLT-3 tyrosine kinase, and as such the tyrosine kinase inhibitor is a staurosporine analogue (such as PKC412 (4-benzyl staurosporine)).

Another embodiment of the invention discloses a method for determining the presence of FLT-3 expression in cells comprising the steps of: (a) incubating the cells for a first time in a saline solution, such as phosphate buffer saline, containing a blocking buffer (such as about 3% fetal bovine serum); (b) incubating the cells a second time in the presence of a first antibody (chosen from the group consisting of anti-FLT-3 antibody and concentration-matched isotype control antibody) diluted in the blocking buffer; (c) incubating the cells a third time in the presence of a second antibody, such as FITC-conjugated secondary antibody; (d) resuspending the cells in a saline solution; and (e) measuring the fluorescence of the cells.

In yet another embodiment, an assay is provided for determining the expression of autophosphorylated FLT-3 in cells comprising the steps of: (a) fixing the cells in about 1% formaldehyde solution; (b) incubating the cells a first time; (c) permeabilizing the cells by suspending the cells in about 90 percent methanol; (d) washing the cells in a Phosphate Buffered Saline (PBS (1×)) containing about 0.5% BSA; (e) incubating the cells a second time in the blocking buffer; (f) adding a first antibody, chosen from the group consisting of monoclonal antibody to autophosphorylated FLT-3 and isotype control antibody, to cells; (g) incubating the cells a third time; (h) washing the cells in a blocking buffer; (i) adding a second antibody, such as the FITC-conjugated secondary antibody, to the cells; and (j) incubating the cells a fourth time.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
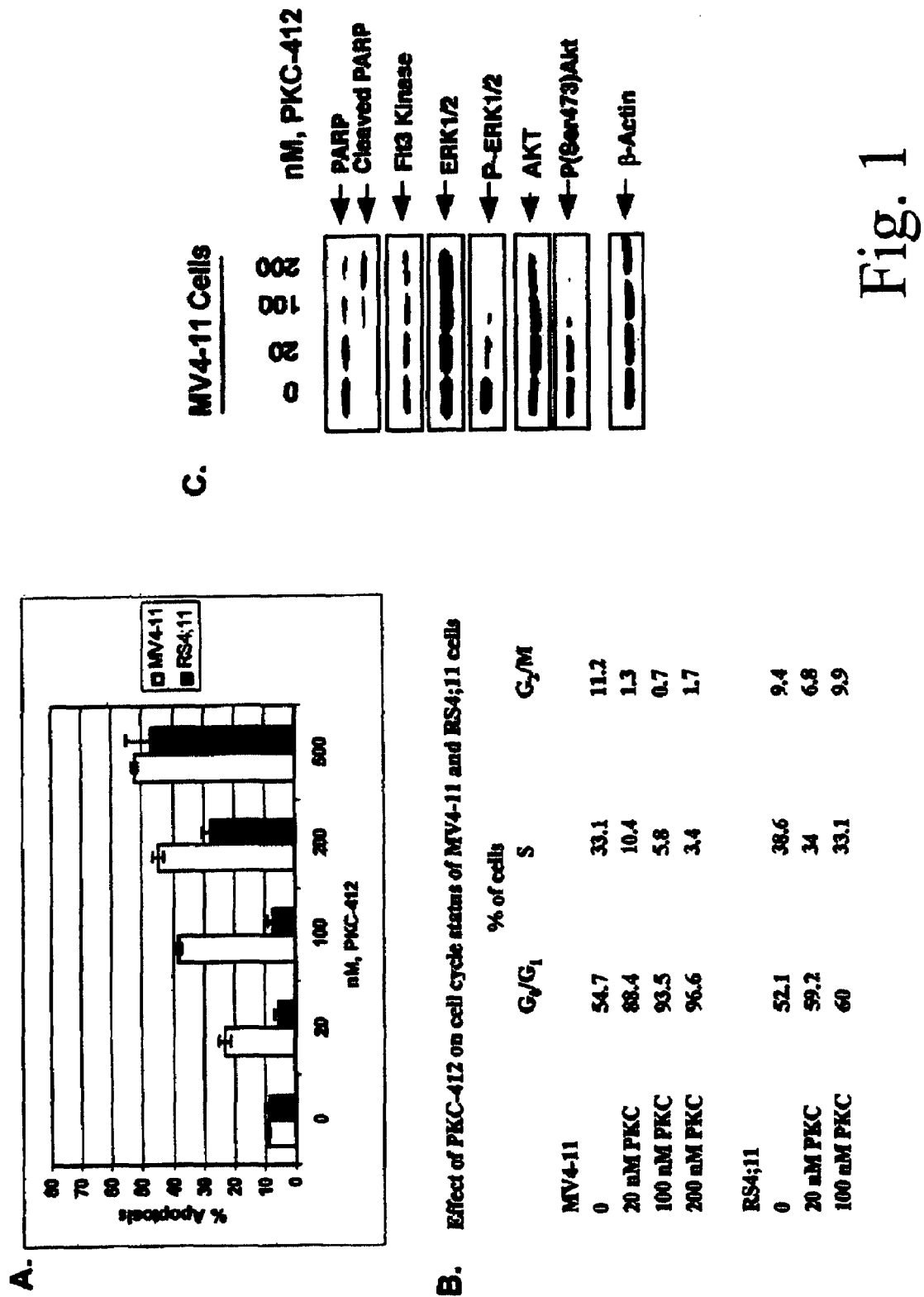
FIG. 1 shows a graph (1A), chart 1(B) and immunoblot (1C) demonstrating the effect of (a.k.a. N-hydroxy-3-[4-[[(2-hydroxyethyl)[2-(1H-indol-3-yl)ethyl]amino]methyl]phenyl]-2(E)-propenamide) PKC412 on cell cycle status and apoptosis of MV4-11 cells.
Figure 2:
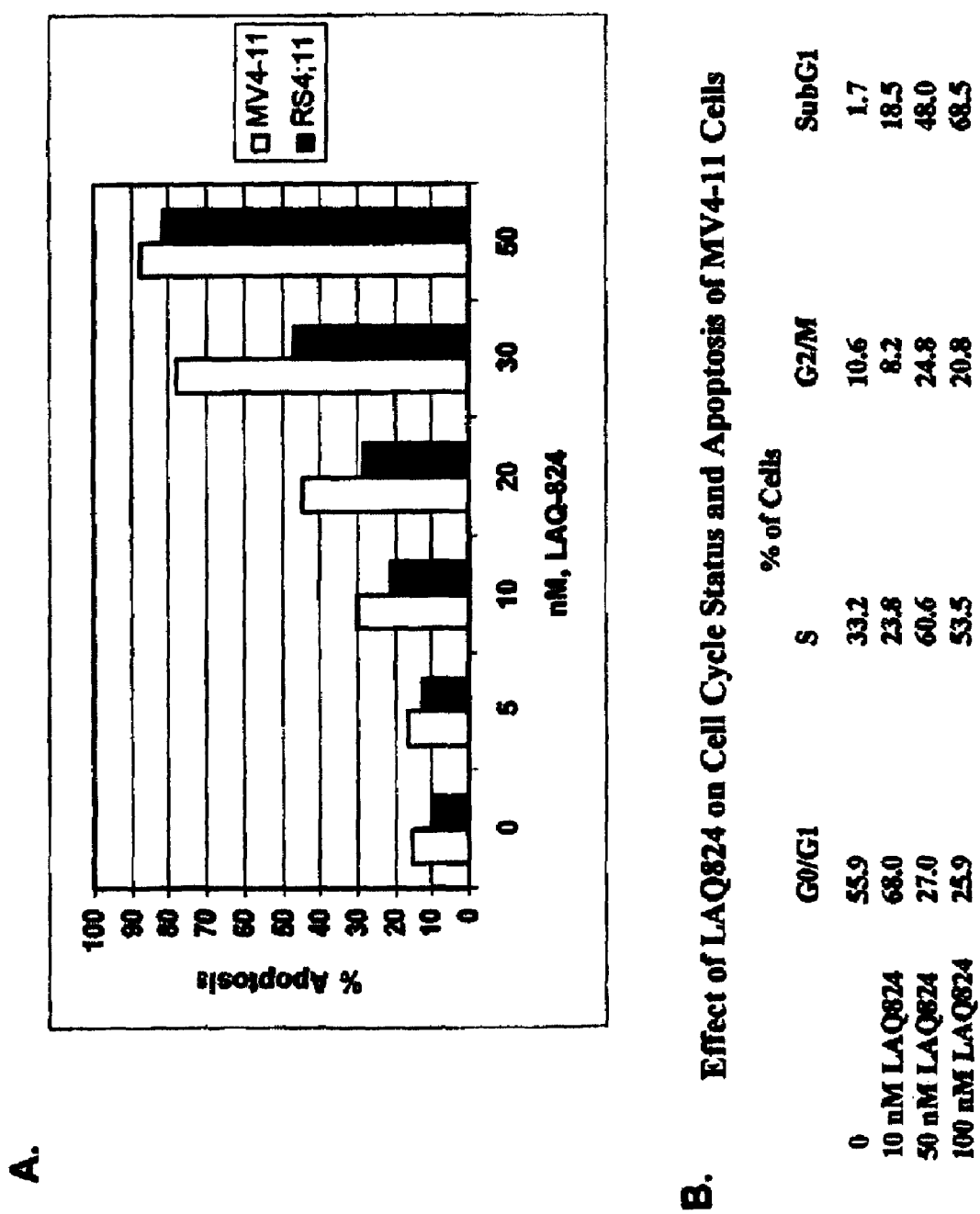
FIG. 2 is a graph (2A) and a chart (2B) indicating LAQ824 induces apoptosis of MV4-11 cells.
Figure 3:
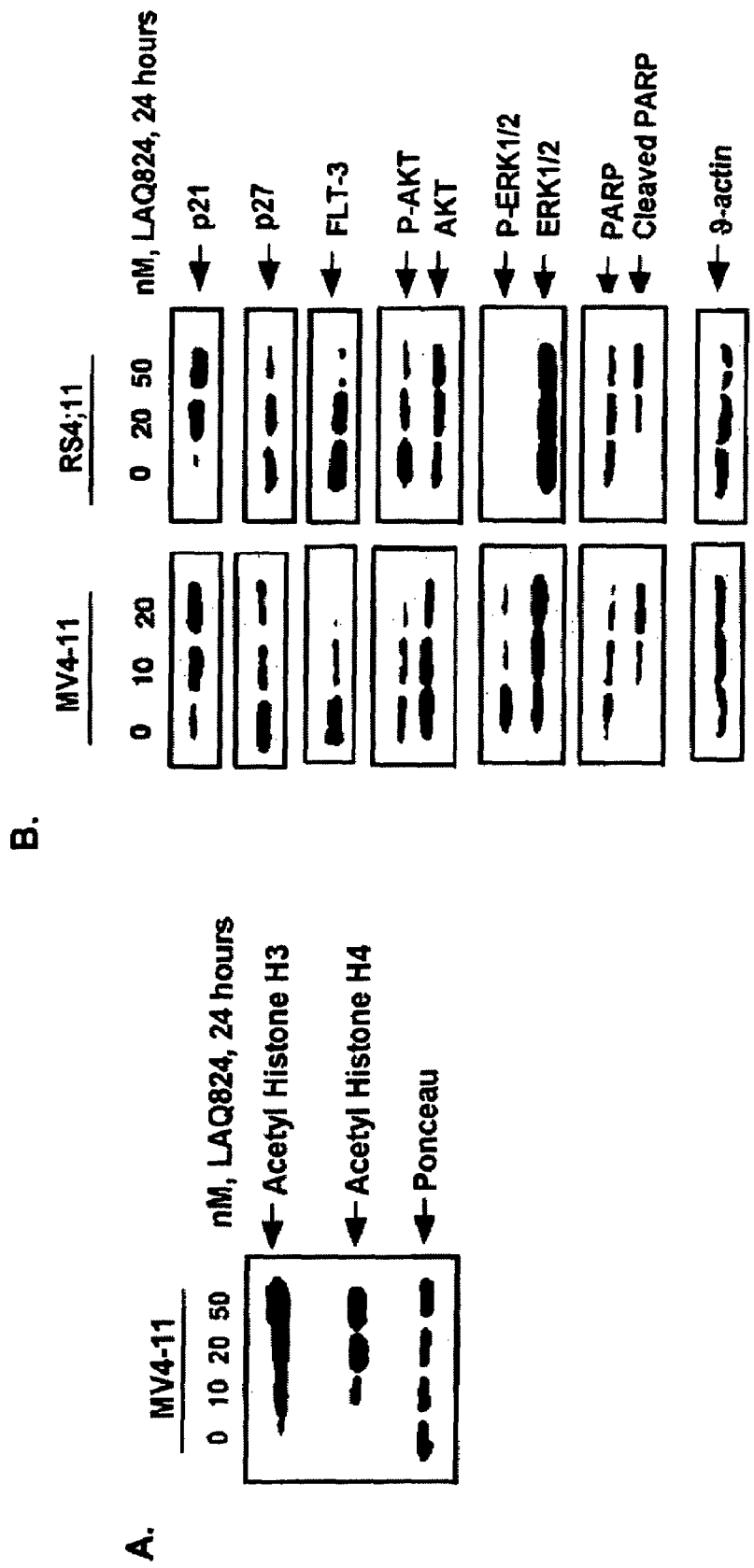
FIG. 3 are immunoblots showing treatment with LAQ824 increases p21, attenuates FLT-3, P-AKT, and P-ERK as well as inducing apoptosis of MV4-11 cells.
Figure 4:
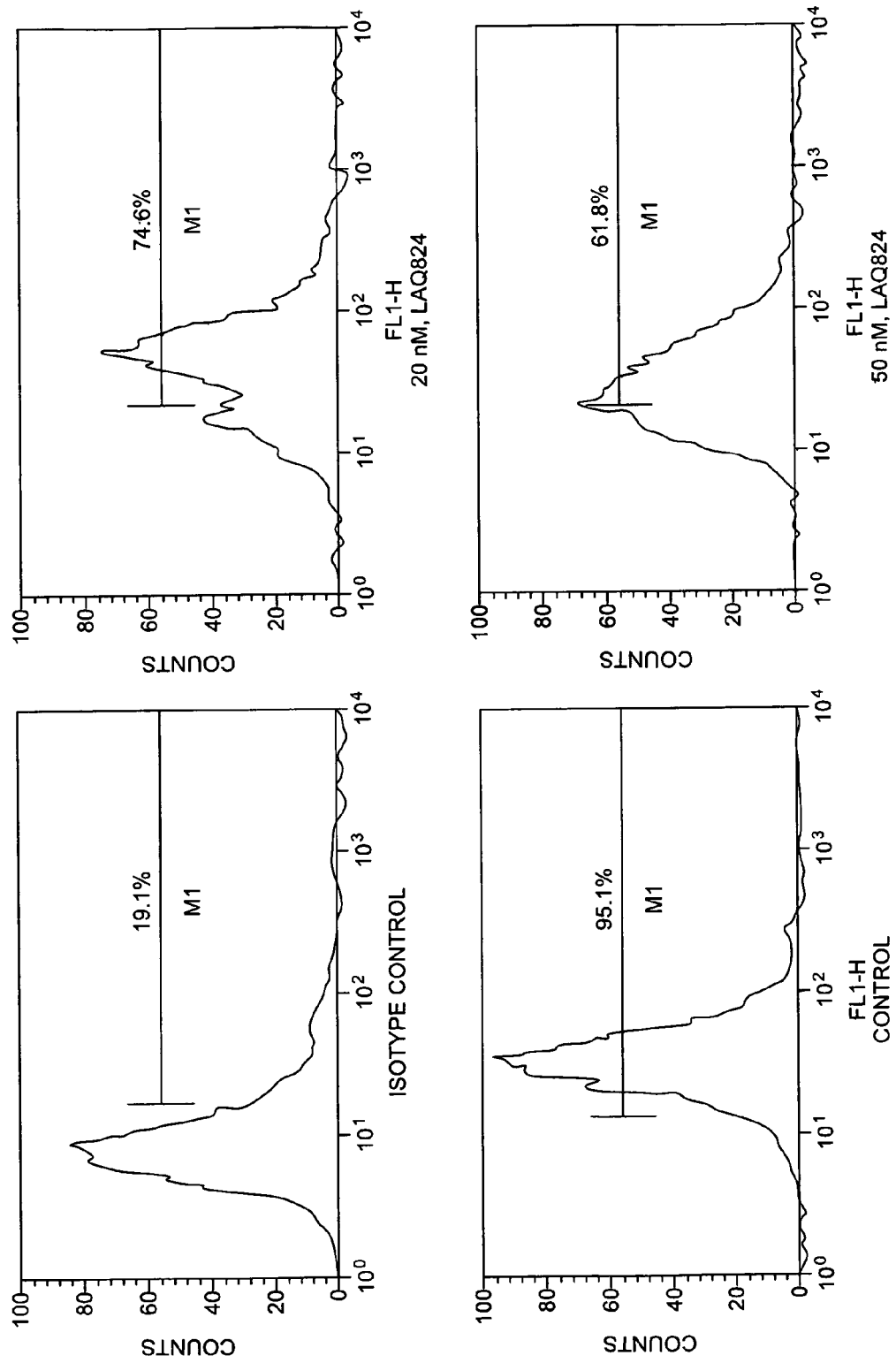
FIG. 4 is a series of graphs showing the effect of LAQ824 on the cell surface expression of FLT-3 kinase in MV4-11 cells.
Figure 5:
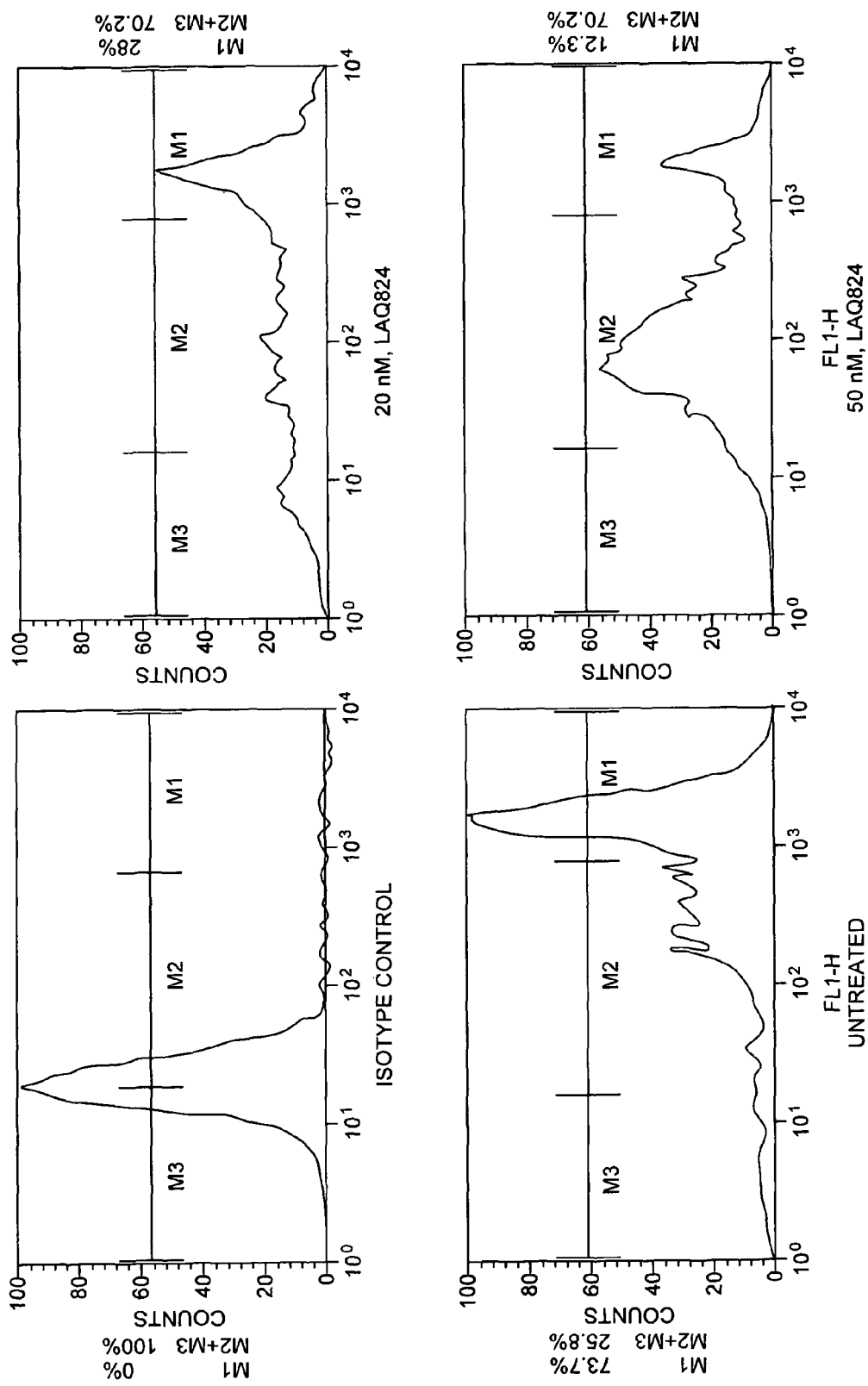
FIG. 5 is a series of graphs showing that LAQ824 attenuates cell surface p-FLY-3 expression in MV4-11 cells.
Figure 6:
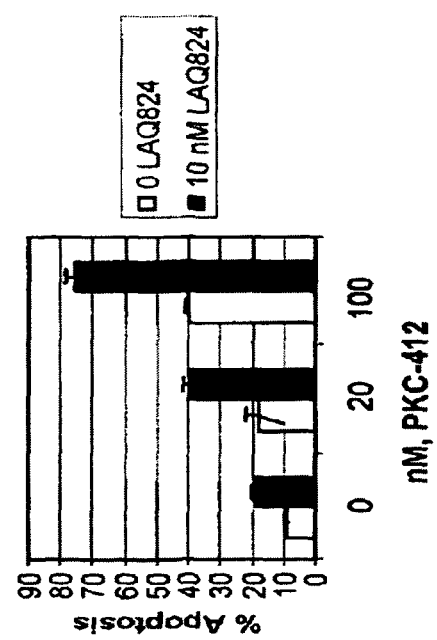
FIG. 6 is a graph (6A) and immunoblot (6B) showing that co-treatment with PKC-412 enhances LAQ824 mediated attenuation of FLT-3 kinase and induction of apoptosis of MV4-11 cells.
Figure 6:
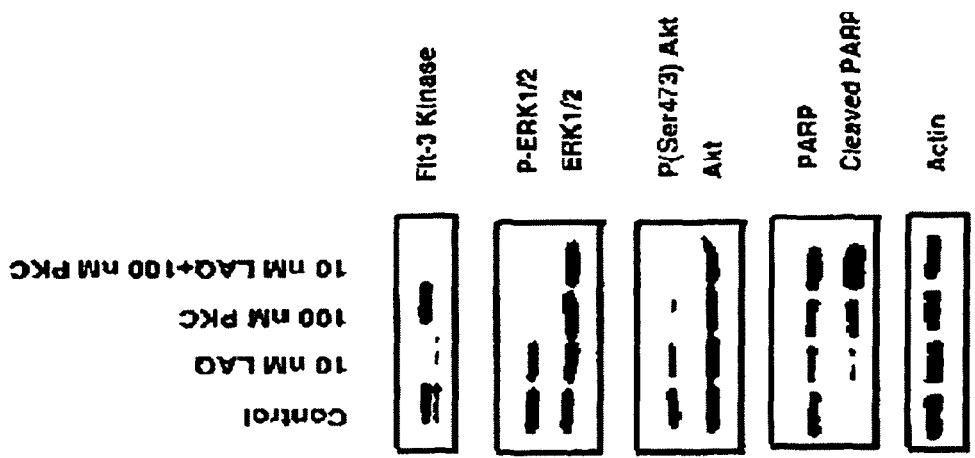

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

A combination of histone deacetylase inhibitor LAQ824 and the FLT-3 kinase inhibitor PKC412 is highly active against human AML cells with constitutively active mutant FLT-3 tyrosine kinase.

Referring now to FIGS. 1 through 6, the present invention discloses that cell cycle effects and apoptosis is induced by the histone deacetylase inhibitor LAQ824 (a cinnamyl hydroxamate) FLT-3 kinase inhibitor PKC412 (4-benzyl staurosporine) against human AML cells that either express the constitutively active mutant or wild type FLT-3 tyrosine kinase. A newly developed flow cytometry (FCM) assay, utilizing anti-FLT-3 or phospho (p)-FLT-3 antibody, was used to demonstrate that while MV4-11 (MV) cells express both FLT-3 and p-FLT-3, RS4-11 (RS) cells only express FLT-3 on their cell surface. Exposure to 20 to 200 nM PKC412 induced cell cycle G1 phase accumulation and, in a dose-dependent manner, significantly more apoptosis of MV than RS cells. This was associated with marked attenuation of p-FLT-3, p-AKT and p-ERK1/2 but not of FLT-3, AKT or ERK1/2 levels, as determined by Western analyses. PKC412 also inhibited the surface expression of p-FLT-3 but not of FLT-3 (determined by FCM) on MV cells. As with other AML cell types, treatment with LAQ824 (10 to 100 nM) induced the acetylation of histone H3 and H4, as well as increased p21 levels. In contrast to PKC412, LAQ824 treatment attenuated both FLT-3 and p-FLT-3 levels in a dose-dependent manner in MV and RS cells, as determined both by Western and FCM analyses. Exposure to LAQ824 (20 to 100 nM) also down regulated the levels of p-FLT-3, p-AKT and p-ERK1/2. Recently, the inventors have demonstrated that treatment with LAQ824 induces acetylation of Hsp-90 and inhibition of its ATP binding and chaperone activities. This results in poly-ubiquitination and proteasomal degradation of the client proteins of Hsp-90, including FLT-3, BcrAbl, AKT and c-Raf. Significantly, co-treatment with LAQ824 and PKC412 induced more apoptosis of MV and RS cells, as compared to treatment with either agent alone. This was associated with more attenuation of p-FLT-3, PAKT and p-ERK1/2 in MV cells. In three samples of primary leukemia blasts with high p-FLT-3 expression from patients with AML in relapse, the combined treatment with LAQ824 and PKC412 again induced more apoptosis and attenuation of p-FLT-3 levels than either agent alone. In conclusion, these studies clearly demonstrate for the first time that a) the combination of LAQ824 and PKC412 may be highly effective in attenuating p-FLT-3, p-AKT and pERK1/2 and in inducing apoptosis of human AML cells with the constitutively active FLT-3 tyrosine kinase, and b) an FCM-based assay may be useful in distinguishing AML with constitutively higher cell surface expression of p-FLT-3 and FLT-3, as well as in assessing the response to inhibitors of p-FLT-3 kinase in AML cells.

Figure 7:
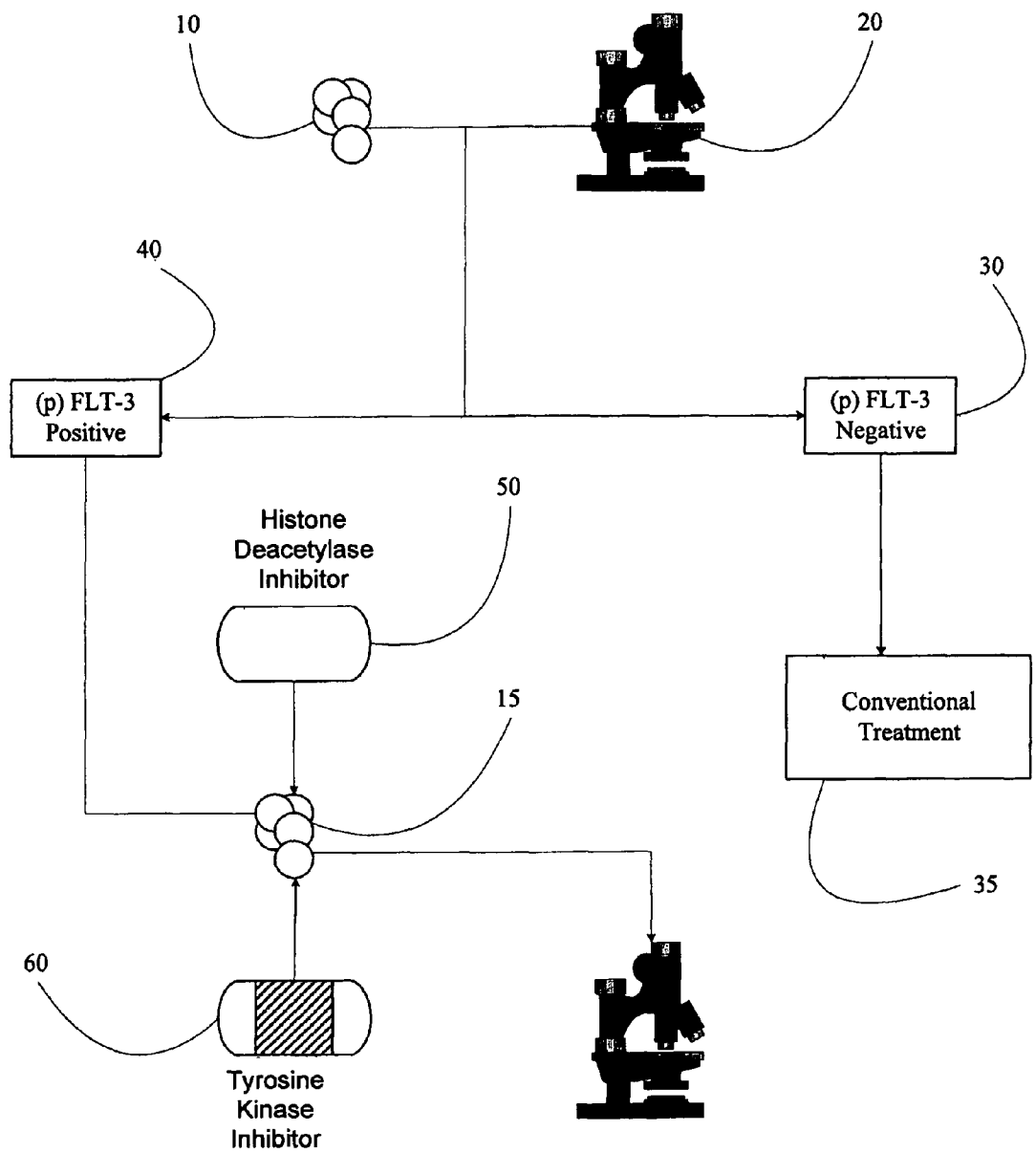
FIG. 7 is a flowchart illustrating the inventive method of treating AML.

Accordingly, the inventive method is illustrated in FIG. 7. A cell sample 10 is taken and assayed to determine the presence of FLT-3 on the surface of the cells 20. If the cells do not express FLT-3 30, then conventional treatment is administered to the patient 35. If the cell sample 10 is positive for the expression of FLT-3 40, target cells 15 are concomitantly treated with a histone deacetylase inhibitor 50 and a tyrosine kinase inhibitor 60 as discussed supra. After treatment cell samples are taken from the patient to determine the effectiveness of the treatment.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin EW [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of the histone deacetylase inhibitor, tyrosine kinase inhibitor, or any combination thereof is administered and dosed in accordance with good medical practice, taking into account the clinical condition of the individual patient, the site and method of administration, scheduling of administration, patient age, sex, body weight, and other factors known to medical practitioners.

The pharmaceutically "effective amount" for purposes herein is thus determined by such considerations as are known in the art.

A therapeutically effective amount of the histone deacetylase inhibitor, tyrosine kinase inhibitor, or any combination thereof is that amount necessary to provide a therapeutically effective amount of the compound in vivo. The amount of the histone deacetylase inhibitor, tyrosine kinase inhibitor, or any combination thereof must be effective to achieve a response, including but not limited to total prevention of (e.g., protection against), improved survival rate or more rapid recovery, or improvement or elimination of symptoms associated with leukemia or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

Administering or Contacting—as used herein refers to the process of delivering to a cell, ex vivo, or a host, in vivo, a therapeutic substance, or a combination of several therapeutic substances. The process can include any method known in the art and is dependent on the type of substance or substances administered. Possible methods include, but are not limited to, parenteral (i.e. subcutaneously, intravenously, intramuscularly, intra-arterially, and direct injection into a tissue or organ), mucosal (i.e. intranasally), pulmonary (i.e. via inhalation), topical, via catheter (i.e. iontopheretically) or orally. Administration is usually achieved via a pharmaceutically acceptable carrier.

Simultaneous measurement of surface FLT-3 kinase and Phospho (P Y591) FLT-3 kinase in Acute Leukemic cells using a flow cytometric assay.

Leukemic cells are harvested by spinning at 1000 rpm at 4 deg for 5 minutes. The cells are washed twice with cold PBS (1×). Equal numbers of cells are utilized for FLT-3 and p-FLT-3 analyses.

Example 1

Figure 8:
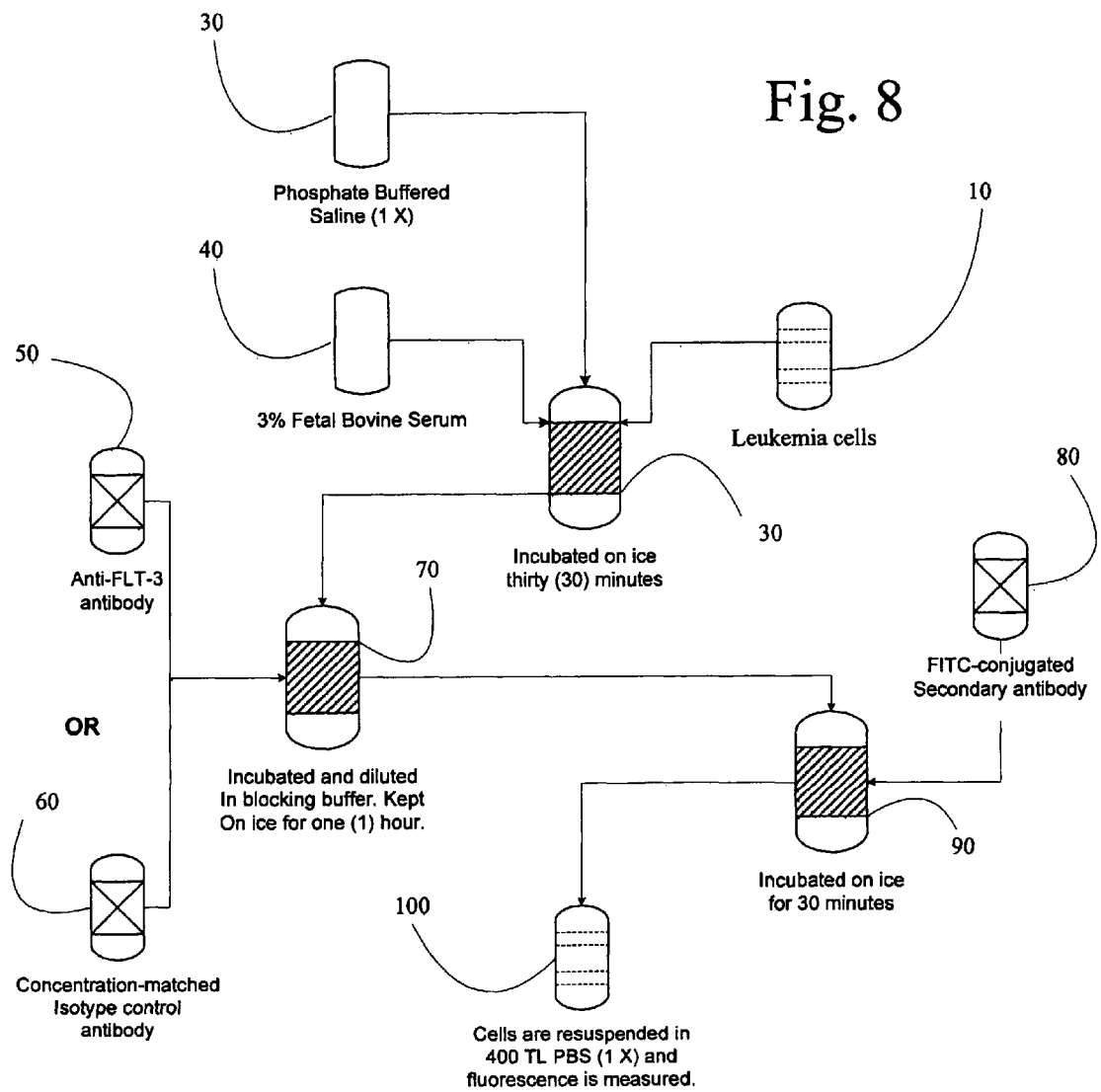
FIG. 8 is a flowchart illustrating the inventive assay for detecting the expression of FLT-3 on the surface of target cells.

In the assay to detect surface FLT-3 expression, shown in FIG. 8, the cells 10 are incubated on ice for thirty minutes 20 in PBS (1×) 30 containing 3% FBS (blocking buffer) 40. Subsequently, the cells are washed twice with cold PBS (1×). Cells are then incubated with either 0.2 Tg of anti-FLT-3 antibody 50 (sc-19635, Santa Cruz Biotechnology, Calif.) or concentration-matched isotype, control antibody (IgG1, Caltag, Burlingame, Calif.) 60 diluted in the blocking buffer and kept on ice for one hour 70. Cells are then washed twice in PBS (1×) and incubated in FITC-conjugated secondary antibody (Molecular Probes, Eugene, Oreg.) 80 for additional thirty minutes on ice 90. The cells are then rinsed twice with PBS (1×) and resuspended in 400 TL PBS (1×) 100. The fluorescence is measured by FACScan Cytometer (San Jose, Calif.).

Example 2

Figure 9:
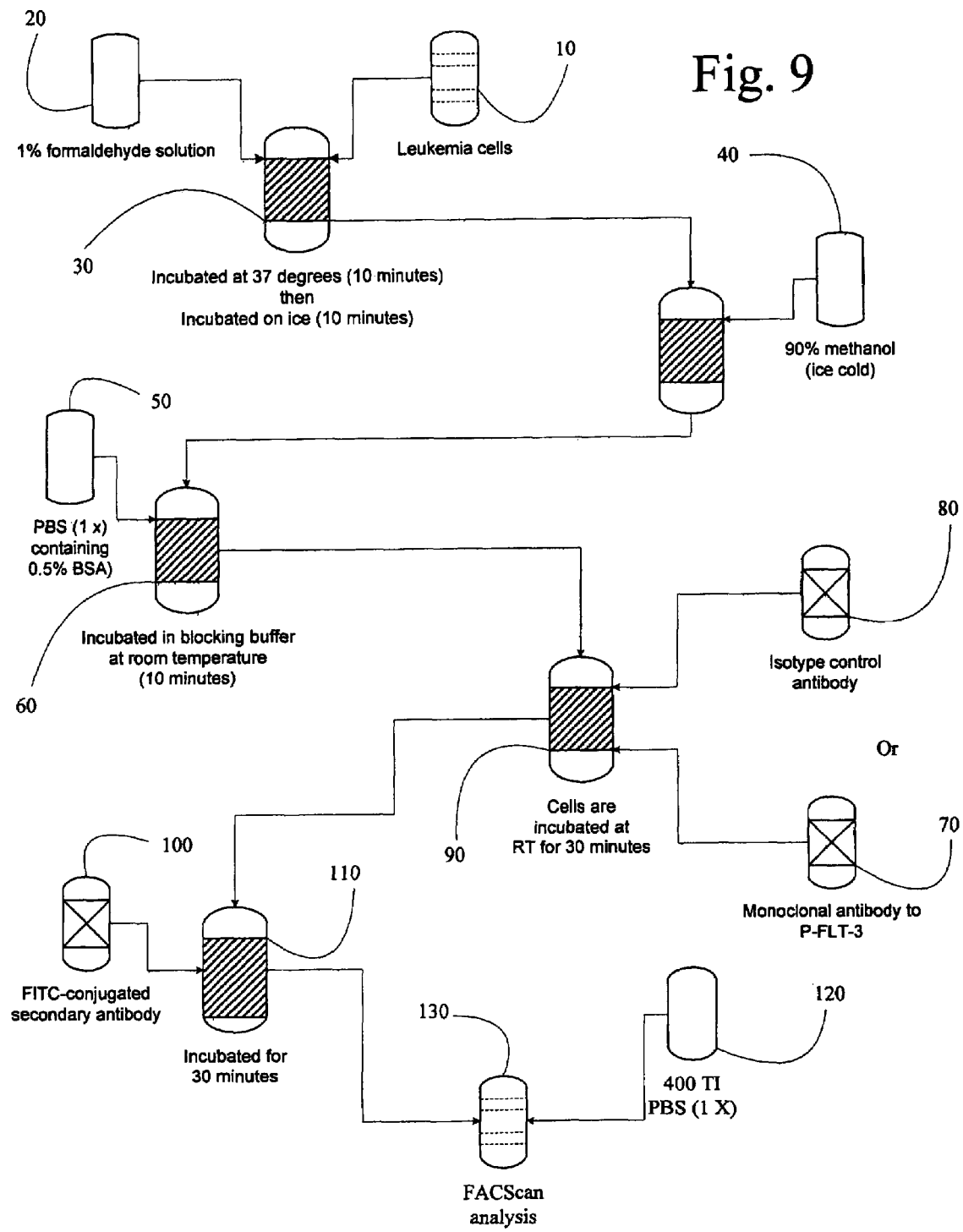
FIG. 9 is a flowchart illustrating the inventive assay for detecting the expression of autophosphorylated (p) FLT-3 on the surface of target cells.

To determine the p-FLT-3 expression, leukemia cells are fixed and permeabilized. Referring now to the flowchart in FIG. 9, cells 10 are fixed in 1% formaldehyde 20 at 37 degrees for ten minutes 30, followed by incubation on ice for ten minutes. Cells are then spun down and permeabilized by resuspending them in ice cold 90% methanol 40 for thirty minutes. Following this, cells are washed twice in the blocking buffer (PBS (1×) containing 0.5% BSA) 50 and then incubated in the blocking buffer for an additional ten minutes at room temperature (RT) 60. Next, to the cells, either 0.4 Tg of monoclonal antibody to p-FLT-3 (Cell Signaling, Beverley, Mass.) 70 or isotype control antibody (IgG2b, Caltag, Burlingame, Calif.) 80 is added and cells are then incubated at RT for thirty minutes 90. Cells are then rinsed twice in the blocking buffer, followed by incubation with the FITC-conjugated secondary antibody (Molecular Probes, Eugene, Oreg.) 100. After thirty minutes of incubation 110, cells are washed twice with PBS (1×) and resuspended in 400 TI of PBS (1×) 120 and analyzed by FACScan 130.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

What is claimed is:

1. A method of treating Acute Myeloid Leukemia comprising the steps of:
    contacting a target cell with a therapeutically effective amount of N-hydroxy-3-[4-[[(2-hydroxyethyl)[2-(1H-indol-3-yl)ethyl]amino]methyl]phenyl]-2(E)-propenamide; and
    concomitantly contacting the target cell with a therapeutically effective amount of 4-benzoyl staurosporine, wherein the target cell expresses constitutively active mutant type or wild type autophosphorylated (p) FLT-3 tyrosine kinase.

2. A method of treating leukemia, the method comprising obtaining a leukemia cell sample from a patient, determining the presence of autophosphorylated (p) FLT-3 tyrosine kinase expression in the cell sample, and concomitantly administering N-hydroxy-3-[4-[[(2-hydroxyethyl)[2-(1H-indol-3-yl) ethyl]amino]methyl]phenyl]-2(E)-propenamide and 4-benzoyl staurosporine to the patient.

3. The method of claim 2 wherein the leukemia is Acute Myeloid Leukemia.

4. A method of treating Acute Myeloid Leukemia in a patient whose leukemia cells express constitutively active mutant type or wild type autophosphorylated (p) FLT-3 tyrosine kinase activity, the method comprising administering to the patient a pharmaceutical composition comprising N-hydroxy-3-[4-[[(2-hydroxyethyl)[2-(1H-indol-3-yl)ethyl] amino]methyl]phenyl]-2(E)-propenamide, 4-benzoyl staurosporine, and a pharmaceutically acceptable carrier.

* * * * *